United States Patent
Kärki (10) Patent No.: US 9,534,988 B2
(45) Date of Patent: Jan. 3, 2017

(54) SAMPLER

(75) Inventor: Pasi Kärki, Kajaani (FI)

(73) Assignee: VALMET AUTOMATION OY, Vantaa (FI)

( * ) Notice: Subject to any disclaimer, the term of this patent is extended or adjusted under 35 U.S.C. 154(b) by 437 days.

(21) Appl. No.: 14/129,131

(22) PCT Filed: Jun. 28, 2012

(86) PCT No.: PCT/FI2012/050679
§ 371 (c)(1),
(2), (4) Date: Dec. 24, 2013

(87) PCT Pub. No.: WO2013/004903
PCT Pub. Date: Jan. 10, 2013

(65) Prior Publication Data
US 2014/0130615 A1    May 15, 2014

(30) Foreign Application Priority Data
Jul. 1, 2011  (FI) .................... 20115703

(51) Int. Cl.
*G01N 1/22* (2006.01)
*F23N 5/00* (2006.01)
*G01N 1/24* (2006.01)

(52) U.S. Cl.
CPC ............ *G01N 1/2202* (2013.01); *F23N 5/003* (2013.01); *G01N 1/2211* (2013.01); *G01N 1/2247* (2013.01); *F23N 2900/05004* (2013.01); *F23N 2900/05005* (2013.01); *G01N 2001/242* (2013.01)

(58) Field of Classification Search
None
See application file for complete search history.

(56) References Cited

U.S. PATENT DOCUMENTS

| | | |
|---|---|---|
| 4,161,883 A | 7/1979 | Laird et al. |
| 4,736,618 A | 4/1988 | Usami et al. |

(Continued)

FOREIGN PATENT DOCUMENTS

| | | |
|---|---|---|
| DE | 29 50 658 A1 | 6/1981 |
| DE | 44 38 267 A1 | 5/1996 |

(Continued)

OTHER PUBLICATIONS

International Search Report issued in International Patent Application No. PCT/FI2012/050679 dated Nov. 1, 2012.

(Continued)

*Primary Examiner* — Robert R Raevis
(74) *Attorney, Agent, or Firm* — Oliff PLC (57) ABSTRACT

A sampler including an ejector and a sample channel extending to the ejector, which are placeable in a mixture of particles of a solid and a medium, the medium being a gas and/or a liquid. The ejector includes at least one inlet and an outlet. The ejector takes a mixture sample by using vacuum via the inlet and discharges it via the outlet so as to make the mixture sample flow from the inlet towards the outlet. The sample channel takes a desired measuring sample from the mixture sample flowing in the ejector, the solid particles and the medium being at least partly separable from one another in the ejector on the basis of the flow and inertia in the mixture sample.

16 Claims, 5 Drawing Sheets (56) References Cited

U.S. PATENT DOCUMENTS

| | | | |
|---|---|---|---|
| 5,423,228 A | 6/1995 | Budd et al. | |
| 6,561,045 B2* | 5/2003 | Liu et al. | 73/863.21 |
| 2001/0032519 A1 | 10/2001 | Liu et al. | |
| 2008/0168752 A1 | 7/2008 | Smith et al. | |
| 2011/0203931 A1* | 8/2011 | Novosselov et al. | 204/600 |

FOREIGN PATENT DOCUMENTS

| | | |
|---|---|---|
| JP | S55-13892 A | 1/1980 |
| JP | U-60-92152 | 6/1985 |
| JP | A-3-277957 | 12/1991 |
| JP | A-9-311098 | 12/1997 |
| SU | 1000832 A1 | 2/1983 |
| SU | 1173302 A1 | 8/1985 |

OTHER PUBLICATIONS

Written Opinion issued in International Patent Application No. PCT/FI2012/050679 dated Nov. 1, 2012.
Search Report issued in Finnish Patent Application No. 20115703 dated Feb. 29, 2012 (with translation).
Apr. 26, 2016 Office Action issued in Russian Application No. 2014103481.
Feb. 9, 2016 Office Action issued in Japanese Patent Application No. 2014-517860.
Apr. 10, 2015 Supplementary Search Report issued in European Application No. 12 80 7918.

\* cited by examiner

SAMPLER

FIELD

The invention relates to a sampler for sampling a mixture of a medium and particles of a solid.

BACKGROUND

When a combustible substance is burned, the quality of burning may be measured by sampling a combustion gas in the combustion chamber, the combustion gas being a heterogeneous mixture of a continuous gas phase and solid particles, and by measuring the amount of one or more substances in the sample, for instance, as a concentration. The gas phase generally comprises various gases produced in the combustion and gases entered into the combustion chamber from the environment.

The sampler may comprise, for instance, a probe locating in the combustion chamber and a pipe between the probe and a measuring part. A sample may be sucked by vacuum into the probe in the combustion chamber, wherefrom the pipe conveys the sample into the measuring part. Because the gas phase, especially, indicates the quality of combustion, the probe includes a filter that prevents access of at least major particles into the measurement. In addition, the filter prevents particles from blocking the pipe and the measuring part.

Sampling involves problems, however. Particles adhere to the filter in the probe all the time, whereby filtering capacity of the filter changes. This may change the measurement result constantly, and consequently it is difficult to obtain reliable information on the action of the combustion process. In addition, the filter may be blocked quickly, and it does not allow a gas sample to pass through at all, or only to an excessively small extent, and therefore the filter has to be replaced frequently. Replacing may be cumbersome, however, and it may require that the combustion process be extinguished. Even though the combustion process would not have to be extinguished, the filter replacement interrupts sampling and measuring, and thus prevents continuous sampling and measuring of the combustion process.

The replacement interval of the filters may be prolonged by cleaning the filters. Even though it may not be necessary to displace the filter for cleaning it, but the filter may be cleaned, for instance, by pressurized gas against the sampling, yet the cleaning operation interrupts the sampling and the measurement frequently.

On account of the above, there is a need for improved sampling of a heterogeneous mixture containing a gas phase and particles of a solid.

BRIEF DESCRIPTION

It is an object of the invention to provide an improved sampler. This is achieved by a sampler of claim 1.

The invention relates to a method for sampling in accordance with claim 9.

Preferred embodiments of the invention are disclosed in the dependent claims.

The sampler of the invention provides several advantages. No separate filter is needed for filtering a mixture sample to be introduced into an ejector, which enables continuous sampling. Thus, there is no need for cleaning and/or replacing the filters either.

LIST OF FIGURES

The invention will now be described in greater detail by means of preferred embodiments, with reference to the accompanying drawings, in which.

DESCRIPTION OF EMBODIMENTS

As regards FIGS. 1A to 4, the following applies in common. The sampler comprises an ejector 100 and a sample channel 112 extending to the ejector 100, which are placeable in a mixture 102 of particles of a solid and a medium, in which the medium may be a gas and/or a liquid. Each particle of the solid particles may comprise one or more substances and the composition of various particles may be identical or different. The ejector 100, in turn, comprises at least one inlet 108 and outlet 116, which may comprise one or more holes for discharging a fluid 118 generating vacuum out of the ejector 100. By means of the vacuum the ejector 100 takes, via at least one inlet 108, a mixture sample 110, which allows a desired measuring sample 122 to be taken by the sample channel 112. The ejector 100 discharges the remaining mixture sample 110 via at least one outlet 116 into the mixture 102. To put it more precisely, the mixture sample 110 may flow in the ejector 100 from the inlet 108 towards the outlet 116, whereby the sample channel 112 is able to take a desired measuring sample 122 from the mixture sample 110 flowing in the ejector 100. The desired measuring sample 122 is possible, because the particles of the solid and the gas or liquid phase separate at least partly from one another in the ejector 100 due to flow and inertia.

The ejector 100 acting as the probe in the sampler and the sample channel 112 extending thereto may be placed in a heterogeneous mixture 102 of a gas phase and particles of a solid. The ejector 100 may also be placed in a heterogeneous mixture 102 of a liquid phase and particles of a solid. The mixture 102 may contain e.g. smoke, dust, ash, sand, air or the like. The sampler may sample smoke, for instance, in such a manner that the ejector 100 and the sample channel 112 extending thereto are in the combustion chamber where the combustion reaction takes place. In a combustion reaction, a combustible substance reacts with oxygen, which releases thermal energy. Therefore, it may be very hot in the combustion chamber, e.g. over 100° C. or even over 1000° C. Despite the heat, separation of the solid particles and the medium and sampling may be carried out in the combustion temperature.

The sampler may also be used in dusty processes, other than combustion chambers, for taking measuring samples. In addition, apart from gas, a liquid is also a possible medium for particles of a solid. The mixture sample 110 may be, for instance, sludge wherefrom the amount of solid particles may be reduced, or the size distribution of solid particles may be altered in the ejector 100 on the basis of flow and inertia.

In the following, embodiments are described using a mixture of solid particles and a gas as an example.

Figure 1A:
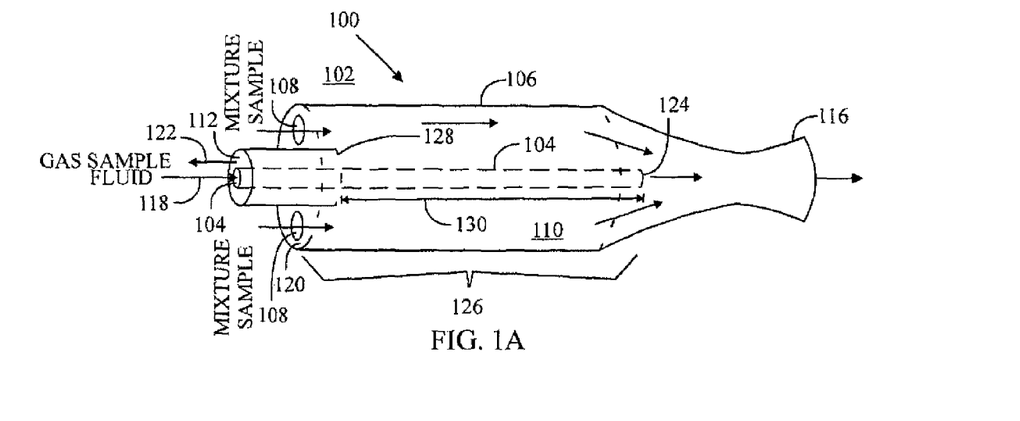
FIG. 1A shows an ejector, at an end of which there is at least one inlet for a mixture sample.

FIG. 1A shows an ejector 100, inside which it is possible to provide vacuum by feeding a fluid 118 through an inner pipe 104 inside the ejector 100 to a second end of an outer pipe 106 of the ejector 100. The cross-sections of the inner pipe 104 and the outer pipe 106 may be e.g. circular, elliptical, triangular, square, rectangular or polygonal of some kind. The fluid 118 generating vacuum is discharged, via the outlet 116, into the mixture 102. Thus, the ejector 100 lets the fluid flow pass through, which fluid flow provides low pressure inside the outer pipe 106 of the ejector 100. The fluid 118 generating vacuum may be e.g. water, air or inert gas. The ejector 100 samples the mixture 102 of solid particles and gas phase surrounding the ejector by drawing the mixture sample 110 via the inlet 108 into outer pipe 106 utilizing the vacuum. The ejector 100 discharges the mixture sample 110 along with the vacuum-generating fluid 118 though the outlet 116. The flow rate of the mixture sample 110 in the ejector 100 may be 10 m/s, for instance.

The sample channel 112 of the sampler, which may also be a pipe connected to the outer pipe 106 of the ejector 100, takes a measuring sample 122 of the mixture sample 110 locating inside the outer pipe 106. The measuring sample 122 may be taken, for instance, by means of partial vacuum that draws the measuring sample 122 from the mixture sample 110 into the sample channel 112. The vacuum in the sample channel 112 exceeds the vacuum produced by the ejector 100, which means that the pressure in the sample channel 112 is lower than in the ejector 100.

The sample channel 112 is employed to take a desired measuring sample 122 of the mixture sample 110 flowing inside the ejector 100 into the sample channel 112. The desired measuring sample 122 may refer, for instance, to the fact that the particle size of the solid in the measuring sample 122 is smaller than a predetermined limit size. The desired measuring sample may also refer, for instance, to the fact that the particle density of the solid in the measuring sample 122 is lower than a predetermined limit density. The desired measuring sample may also refer, for instance, to the fact that the mass of the particles of the solid in the measuring sample 122 is lower than a predetermined limit mass. The desired measuring sample 122 is obtained by separating the particles of the solid and the medium from one another in the ejector 100 on the basis of the flow and inertia of the mixture sample 110. It is possible to affect the characteristics in the solid particles of the measuring sample 122 by how the sample channel 112 is placed in the ejector 100 and by the direction in which the measuring sample 122 is taken in relation to the flow of the mixture sample 110 in the ejector 100.

The sample channel 112 may be placed in the end 120 of the ejector 100 that is opposite to the outlet 116 of the ejector 100. The inner pipe 104 of the ejector 100 extends further than the sample channel 112 inside the outer pipe 106 of the ejector 100. The end 124 of the inner pipe 104 may be fairly close to the outlet 116 inside the outer pipe 106, but the end 128 of the sample channel 112 is not located in the immediate vicinity of the outlet 116. In general, the end 124 of the inner pipe 104 may be located at the point which is between the midway of the outer pipe 106 and the outlet 116. Whereas, in general, the end 128 of the sample channel 112 may be located in an area between the midway of the outer pipe 106 and the end 120.

The space 126 in the outer pipe 106 remaining between the end 124 of the inner pipe 104 and the end 120 contains the mixture sample 110, of which the measuring sample 122 is taken with the sample channel 112, because the sample channel 112 extends to this space 126. Because there is a separating distance 130 between the end 124 of the inner pipe 104 and the end 128 of the sample channel 112, the fluid generating vacuum and discharging from the inner pipe 104 does not mix unintentionally with the measuring sample 122. Thus is obtained a clean measuring sample 122, which is advantageous to accurate measurement.

In the space 126 of the outer pipe 106 between the end 124 of the inner pipe 104 and the end 120 the principal flow direction of the mixture sample 110 is towards the outlet 116 as indicated by the arrows. The flow may be laminar and/or turbulent. The gas in the mixture sample 110 is able, however, to spread in the space 126. The sample channel 112 may suck a measuring sample 122 out of the mixture sample 110 in a direction deviating from the flow direction of the mixture sample 110. In FIGS. 1A to 1D the difference between the principal flow direction of the mixture sample 110 and the flow direction of the measuring sample 122 is largest possible, i.e. 180 degrees. When the flow direction of the measuring sample 122 deviates from that of the mixture sample 110, the distribution of solid particles in the measuring sample 122 is different from the mixture sample 110. This results, for instance, from the fact that the inertia of particles of the solid impedes sudden changes in the direction of motion. The quantity of the measuring sample 122 is generally small compared with the quantity of the mixture sample 110. The measuring sample 122 may be e.g. 50 percent of the quantity of the mixture sample 110. In continuous measurement this means that the amount of the measuring sample flow in the sample channel 112, measured in cubic meters per second ($m^3/s$), is 50 percent. Often the quantity of the measuring sample 122 may be only percents, per milles or even less of the quantity of the mixture sample 110. When the fluid 118 generating vacuum is a gas, the rate of flow into the ejector 100 may be e.g. 125 l/s, i.e. 0.125 $m^3/s$ and the rate of flow of the measuring sample 122 may be e.g. 20 l/s, i.e. 0.02 $m^3/s$.

When the flow direction of the mixture sample 110 and the sampling direction of the measuring sample 122 differ from one another, due to solid particle inertia the particles of the solid tend to continue in their direction of motion towards the outlet 116, but the gas in the mixture sample 110 may more readily change its direction and enter the sample channel 112. The larger the angle between the flow direction of the mixture sample 110 and the flow direction of the measuring sample 122 in the sample channel 112, the more difficult for the solid particle to change its direction of motion and the more unlikely said particle ends up in the sample channel 112. In addition, the larger the mass of the solid particle, the more unlikely said particle will be transferred into the sample channel 112. The likelihood for the solid particle to be included in the measuring sample in the sample channel 112 also reduces as the flow rate of the mixture sample 110 increases. Inertia thus separates the solid particles and the gas from one another and inertia may be utilized in taking the measuring sample 122 into the sample channel 112 in such a manner that solid particles in the measuring sample 122 will be sufficiently or completely avoided. Tiny particles, if there are any in the mixture sample 110, may access the sample channel 112 along with the measuring sample 122.

Because the flow rates of the mixture sample 110 and the measuring sample 122 and/or the angles of flow direction may be set as desired, it is possible to affect the size and/or weight distribution of the solid particles entering the sample channel 112. To put it simply, the place, the flow rate and/or the difference in flow directions may define the threshold mass or threshold size under which particles are allowed in the sample channel 112. It is often desired that the measurement includes tiny solid particles in addition to gas.

When the mixture sample 110 flows without any particular turbulence from the inlet 108 towards the outlet 116 and when the measuring sample 122 is taken of the mixture sample 110, the principle of sampling is similar to that of a virtual impactor, with the exception that in the present solution the sampling is performed on the gas, not on the particles. In addition to the measuring sample, however, it is also possible to take a sample of particles. When mainly a gas sample is measured, blocking and fouling of the measuring devices are avoided. In addition, in the measurement it is possible to eliminate measurement of substances bound to the particles. Further, the concentration of gas to be measured may be determined.

FIG. 1A shows an embodiment comprising two inlets 108 for a mixture sample 110. The inlets 108 may be holes in an end 120 of an ejector 100. In a general case, there may be one or more inlets 108. Different inlets 108 may be holes equal or different in size.

Figure 1B:
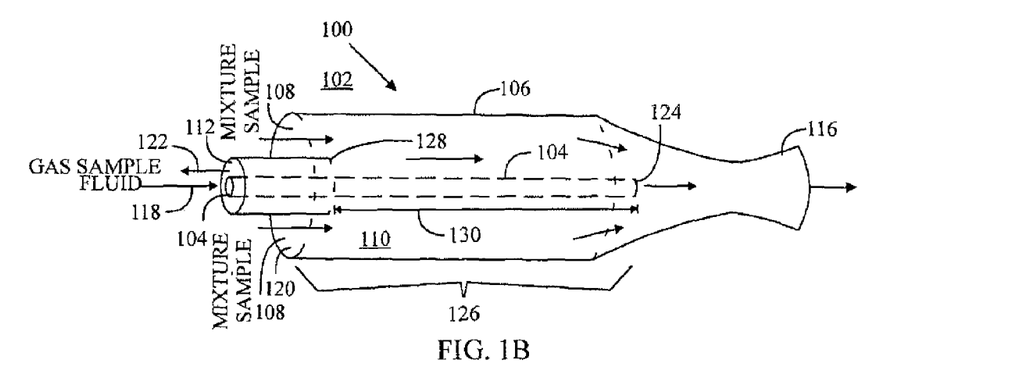
FIG. 1B shows an ejector, whose end is an inlet for a mixture sample.

FIG. 1B shows an embodiment, in which the whole end 120 of the ejector 100 constitutes an inlet 108. Thus, the end 120 does not necessary have any wall or wall-like structure. It is also possible that only a part of the end 120 of the ejector 100 serves as the inlet 108.

Figure 1C:
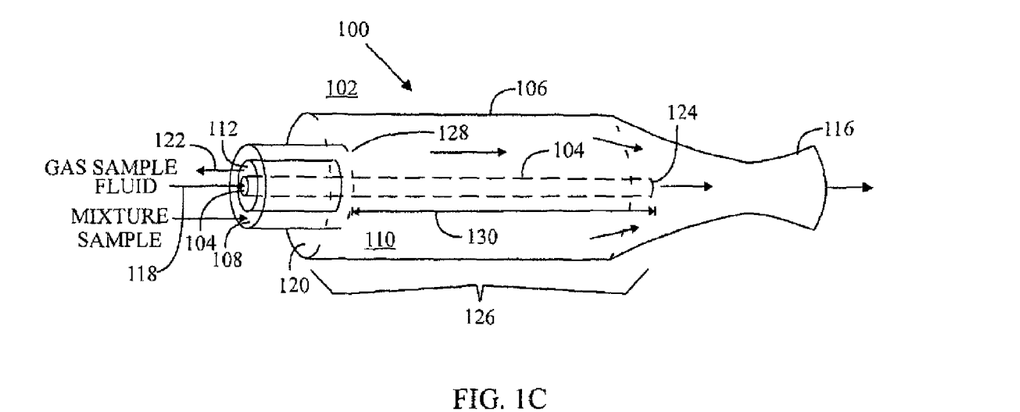
FIG. 1C shows a sampler whose inner pipe, inlet and sample channel are nested.

FIG. 1C shows an embodiment, in which the inlet 108 surrounds an inner pipe 104 and a sample channel 112. The inner pipe 104 may also surround the inlet 108 and the sample channel 112. Alternatively, the sample channel 112 may also surround the inlet 108 and the inner pipe 104. Generally, in a solution like this the inner pipe 104, the inlet 108 and the sample channel 112 are nested. It is also possible that only two of them are nested and one is adjacent thereto.

Figure 1D:
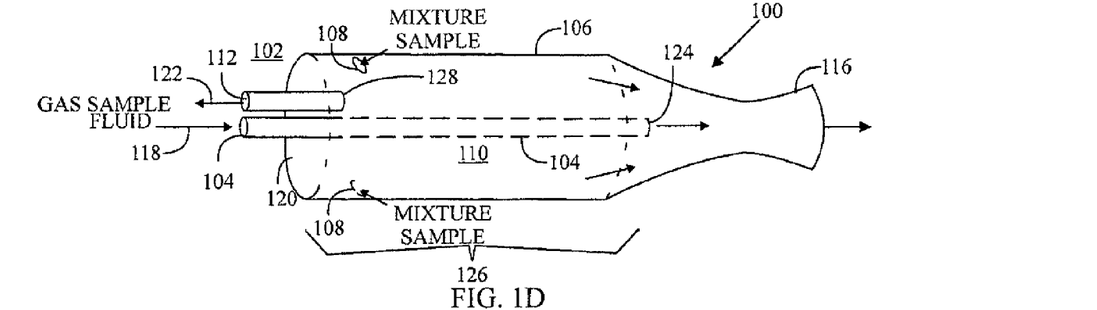
FIG. 1D shows a sampler whose inlet is located in an outer pipe of the ejector.

FIG. 1D shows an embodiment, in which at least one inlet 108 is located in the outer pipe 106 of the ejector 100. Each inlet 108 is located within the area of a space 126. In this embodiment, the flow direction of the mixture sample 110 and the flow direction of sampling the measuring sample 122 are at an angle of 90 degrees to one another. In addition, FIG. 10 shows an embodiment, in which the sample channel 112 is adjacent to the inner pipe 104.

Figure 1E:
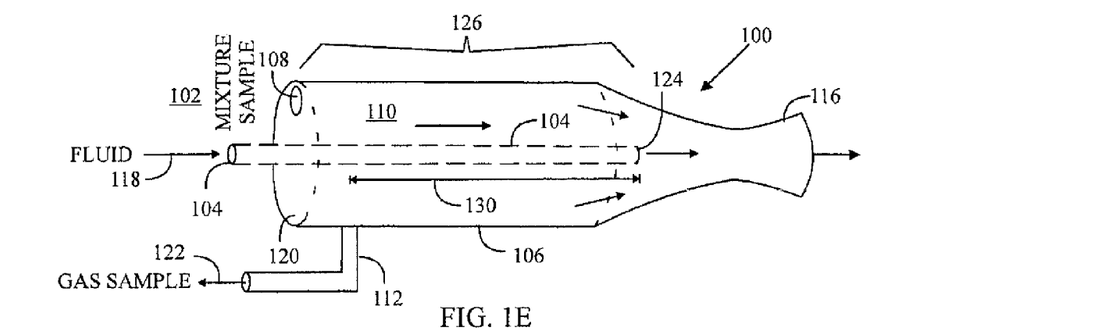
FIG. 1E shows a sampler in which the sample channel is attached to the outer pipe of the ejector.

FIG. 1E shows an embodiment, in which the sample channel 112 is attached to the outer pipe 106 of the ejector 100. In that case the measuring sample 122 may be taken quite in the vicinity of the inner surface of the outer pipe 106 or in the middle of the ejector 100, depending on how deep inside the ejector 100 the sample channel 112 extends. In this embodiment the principal flow direction of the measuring sample 110 and the sampling direction may be at an angle of about 90 degrees to one another.

Figure 2:
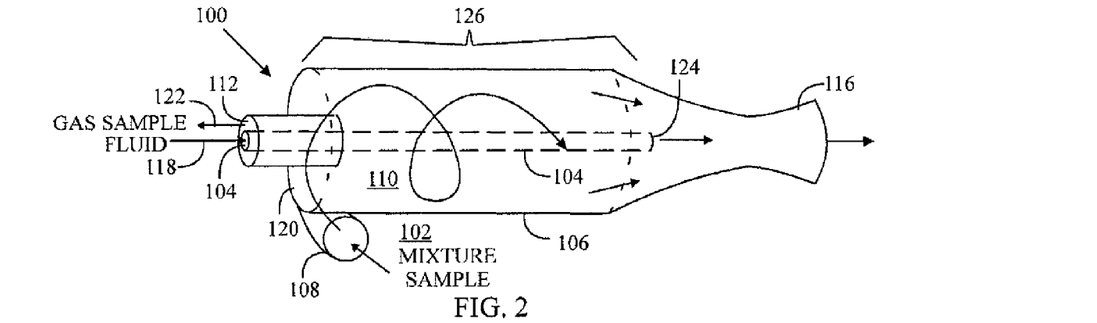
FIG. 2 shows a sampler operating on a cyclone principle.

FIG. 2 shows an embodiment, in which the ejector 100 may operate on a cyclone principle, which is also based on inertia. In the cyclone principle, the gas and the solid particles contained in the mixture sample 110 are brought to spiral-like turbulent motion (spiral line) inside the outer pipe 106 of the ejector 100, until turbulent elements are removed from the ejector 100 back into the mixture 102 along with the fluid 118 that generates vacuum. The turbulent motion separates the solid particles contained in the mixture sample 110 by means of centrifugal force in such a manner that the particles of highest density and largest size appear on the outermost periphery of the turbulent motion. Thus, in the middle of the ejector 100 there will remain gas of the mixture sample 110, wherefrom at least some of the solid particles have been removed. The longer the distance from the longitudinal axis of the ejector 100 towards the surface of the outermost pipe 106, the larger the solid particles likely appearing in the swirling mixture sample 110. The longitudinal axis of the ejector 100 may be the same as the longitudinal axis of the inner pipe 104.

To provide turbulent motion at least one inlet 108 may be a pipe on the outer periphery of the ejector 100, the central axis of the pipe being directed tangentially to the inner surface of the outer pipe 106 of the ejector 100. To place the inlet 108 in the ejector 100 in this manner brings the mixture sample 110 to the turbulent motion in the ejector 100 following the inner surface of the outer pipe 106 of the ejector 100. The mixture sample 110 sampled in the mixture 102 with vacuum by the ejector 100 is thus in turbulent motion about the longitudinal axis of the ejector 100 parallel with the flow-through.

The sampler also comprises a sample channel 112 whereby a measuring sample 122 may be taken, in the direction of the longitudinal axis, in the centre of the ejector 100 where the particles of the mixture sample 110 are smallest. Thus, when the end 128 of the sample channel 122 is placed in the ejector 100 to a location where the turbulent flow of the mixture sample 110 renders the distribution of solid particles different from that elsewhere in the mixture sample 110, the mixture sample 110 may be sampled for a desired measuring sample 122. The desired measuring sample 122 contains solid particles of a desired size. To put it simply, the place, the flow rate and/or the difference in flow directions may define the threshold mass or threshold size under which particles are allowed to drift along with the gas into the sample channel 112.

The sample channel 112 may also be a pipe whose cross section may be the same as that of the inner and outer pipes 104, 106 of the ejector 100. The sample channel 112 may surround the inner pipe 104, i.e. the sample channel 112 and the inner pipe 104 may be nested as shown in FIG. 1A.

FIG. 3 shows an embodiment in which the sample channel 112 may be located in the cross-sectional centre of the ejector 100 and the inner pipe 104 may be adjacent to the sample channel 112. In that case the inner pipe 104 is not in the middle of the ejector 100, in view of the longitudinal axis, not at least in the area where the sample channel 112 is. The inner pipe 104 may be bent, however, after the end of the sample channel 112, to the centre of the of the ejector 100.

In an embodiment the measuring sample 122 is not necessarily diluted with any fluid prior to measurement. Undilutedness enables elimination of errors resulting from dilution in the measurement. In fact, it will be sufficient for the measurement that the temperature of the measuring sample 122 can be lowered to an appropriate measuring temperature during the sample transfer. An appropriate measuring temperature may be, for instance, a water boiling temperature or a temperature below that. In particular, an undiluted measuring sample 122 can be measured for moisture in the measuring sample 122, for instance. Yet, it is also possible to measure a diluted measuring sample 122 for moisture.

Figure 4:
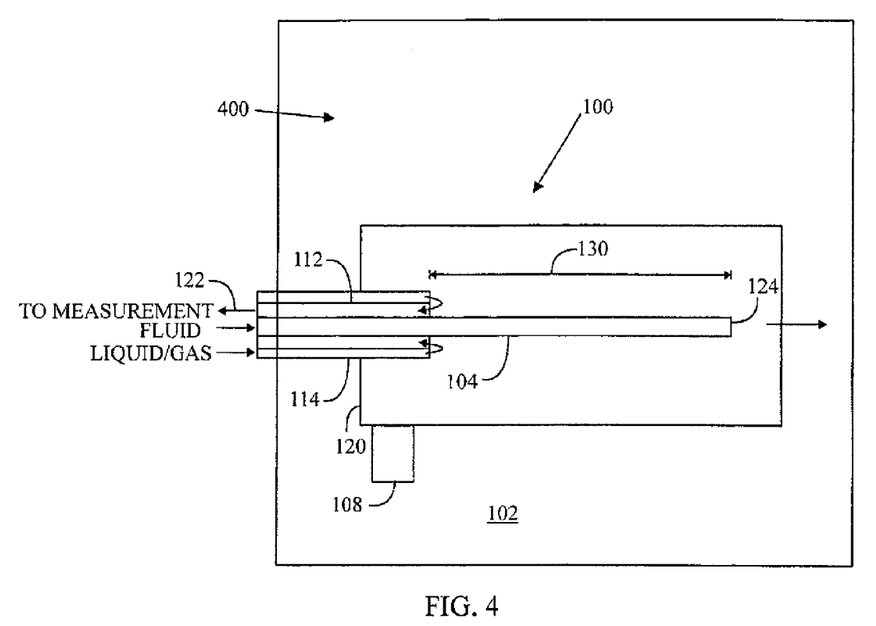
FIG. 4 shows a sampler including a fluid channel for mixing a dilution fluid into a measuring sample.

FIG. 4 shows an embodiment, in which the sampler may further comprise a fluid channel 114. The fluid channel 114 may feed dilution fluid into the sample channel 112, whereby the taken measuring sample 122 and the dilution fluid mix before measurement. The dilution fluid in the fluid channel 114 may be water or inert gas, for instance. The dilution fluid may be cold, e.g. below 0° C., at room temperature, i.e. about 20° C., or it may be heated e.g. to tens or hundreds of centigrades, which may have an effect, for instance, in pre-treatment of a combustion gas sample 122. By means of the dilution fluid flowing in the fluid channel 114 it is possible to mix the gas sample 122 with the dilution fluid immediately upon sampling in the combustion chamber, or in the immediate vicinity thereof.

In FIG. 4 the sampler is placed in the combustion chamber 400. In that case the ejector 100 may be from the ejector end 120 up to the outlet 116 of the ejector 100 in the combustion chamber 400 while only the pipes 104, 112 and 114 may extend from the ejector 100 to the outside of the combustion chamber 400 so as to enable the operation of the ejector 100 and the sampling. The sampler may be attached to a wall of the combustion chamber 400 by its pipes and/or the ejector end 120, for instance, through a simple flange attachment, which requires one hole in the wall of the combustion chamber 400. In addition to or in place of the flange attachment, the attachment may also be implemented as a simple threaded connection, which also requires just one hole in the wall of the combustion chamber 400. A low number of holes in the wall of the combustion chamber 400 is advantageous, because in this manner it is possible to reduce leaks and corrosion, for instance.

Figure 3:
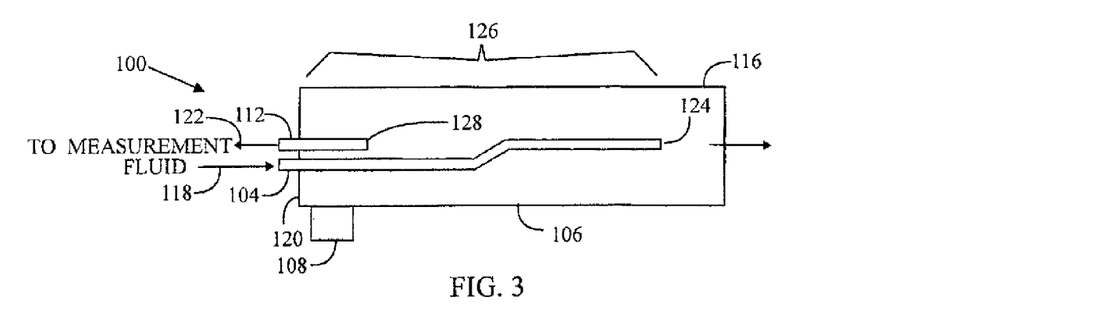
FIG. 3 shows an ejector having a sample channel in the middle of the ejector and an inner pipe adjacent to the sample channel.

In the case of other FIGS. 1 to 3 as well, the sampler may be in the combustion chamber 400. A gas sample 122 taken in the combustion chamber 400 may contain solid particles. For instance, in a measuring sample taken from a soda recovery boiler the particle size of a solid may generally remain such that the particles are less than 10 μm in diameter.

In an embodiment the combustion chamber 400 is a steam turbine boiler.

In an embodiment the combustion chamber 400 is a boiler which burns cooking liquor used in pulp making. The cooking liquor to be burnt may be e.g. black lye or the like.

In an embodiment the combustion chamber 400 may be a boiler of a heat distribution centre.

In an embodiment the combustion chamber 400 is a lime sludge reburning kiln.

The measurement may be carried out in such a manner that a measuring sample 122 is transferred along the sample channel 112 to a measuring part, for instance, where optical, chemical and/or other measurements may be performed to find out the properties of the mixture. The direction of transfer in the sample channel may be opposite to the feed direction of the fluid 118 generating vacuum.

Figure 5:
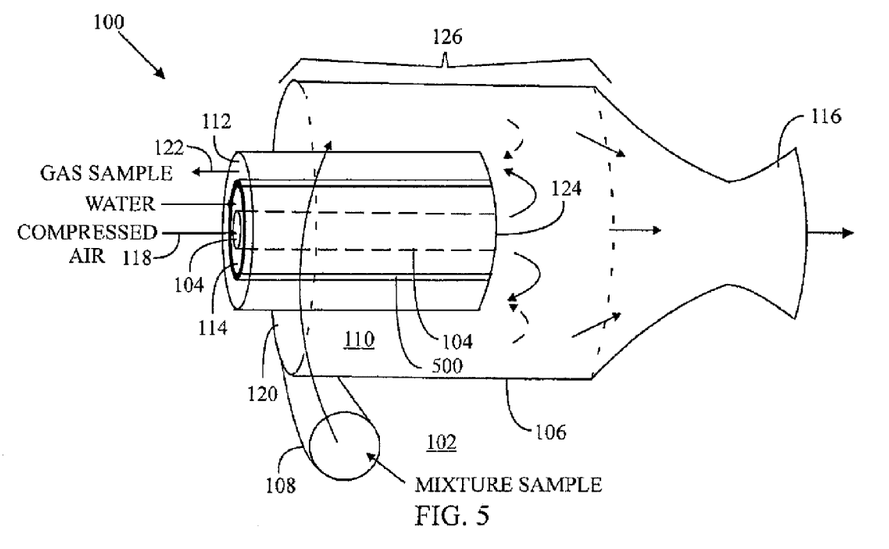
FIG. 5 shows a sampler in which the inner pipe is separated from the sample channel for a gas sample by a fluid channel.

FIG. 5 shows a sampler in which an inner pipe 104 is separated from the sample channel 112 for a gas sample by a fluid channel 114. The fluid channel 114 may serve as thermal insulation between the sample channel 112 and the inner pipe 104. The material of the wall 500 of the fluid channel 114 may be thermally insulating or resistant to even high temperatures. The wall 500 may be filled with gas, for instance. The gas may be air or a gas that is inert in the heat and/or in the combustion chamber 400. The space forming the wall 500 may also be a channel for flowing, hot gas, for instance, whereby the gas sample will not cool down in the sample channel 112. These structural solutions enable the taken sample to be maintained in the sample channel 112 as hot as possible prior to its measurement analysis, which increases the accuracy of measurement. Otherwise, for instance, cold, compressed air in the inner pipe 104 may cool down the sample in the sample channel 112, whereby part of the sample may condense onto the surface of the sample channel 112 and be omitted from the measurement analysis.

Figure 6:
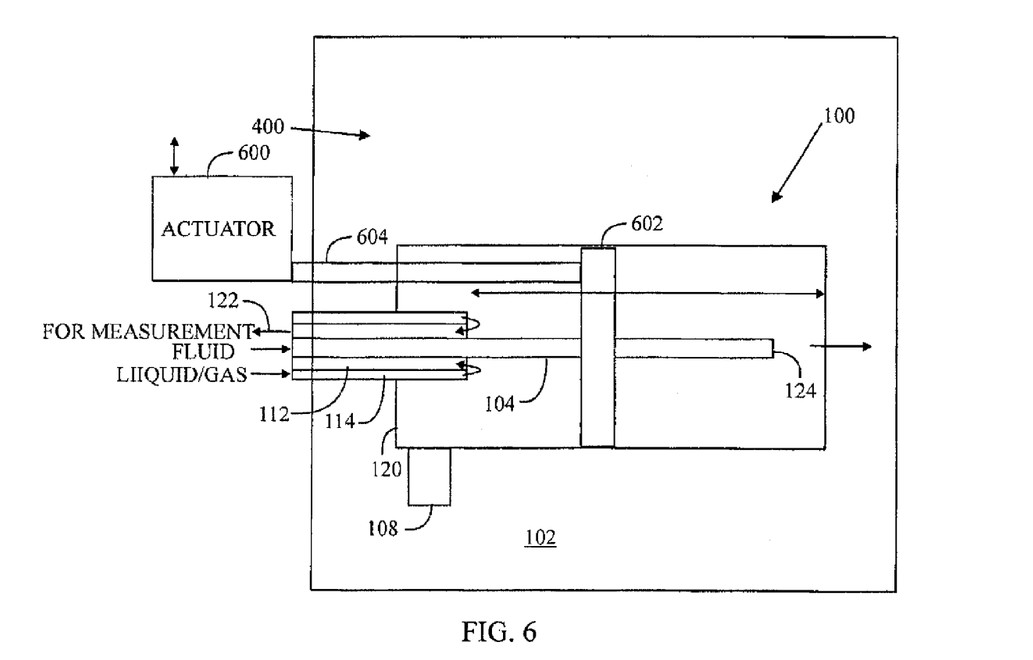
FIG. 6 shows the sampler in a combustion chamber.

FIG. 6 shows the sampler in a combustion chamber 400. The sampler may comprise an actuator 600 which is outside the combustion chamber 400 but which has a mechanical connection 604 to a piston 602 inside the outer pipe 106 of the ejector 100. The actuator 600, which may be a motor, for instance, moves the piston 602 inside the ejector 100 in a reciprocating manner (cf. arrow) transmitted by the mechanical connection 604. The piston 602 may thus clean the inner surface of the outer pipe 106 of the ejector 100 for dirt that may adhere thereto from combustion gases, for instance. The actuator 600 may comprise, for instance, an electric motor and the actuator 600 may receive signals controlling the cleaning of the ejector 100 from an external controller. The actuator 600 itself may also comprise a controller that controls cleaning. The cleaning of the ejector 100 may be performed regularly or according to how fouling the gases in the combustion chamber are assessed or measured to be.

Figure 7A:
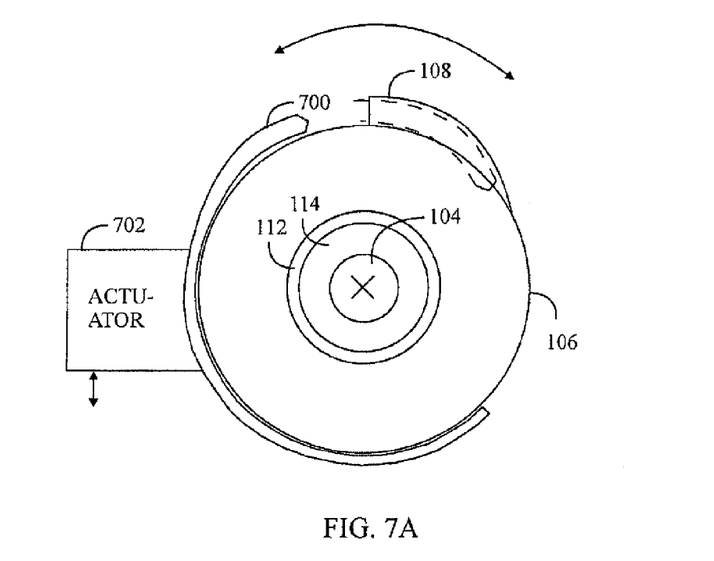
FIG. 7A shows an inlet cleaning mechanism, seen from the ejector end.

FIG. 7A shows a cleaning mechanism of the inlet 108, seen from the ejector end, The actuator 702, which may be a motor, may move a projection 700 in a reciprocating manner such that the projection 700 may penetrate into the inlet 108 and retract therefrom. A dashed line inside the inlet 108 represents the projection 700 in the inlet 108. Thus the inlet 108 and a passage into the ejector 100 will not be fouled or blocked. The actuator 702 may comprise an electric motor, for instance. The actuator 702 may receive signals controlling the cleaning of the inlet 108 from an external controller. The actuator 702 itself may also comprise a controller that controls cleaning. The cleaning of the inlet 108 may be performed regularly or according to how fouling the gases in the combustion chamber are assessed or measured to be.

Figure 7B:
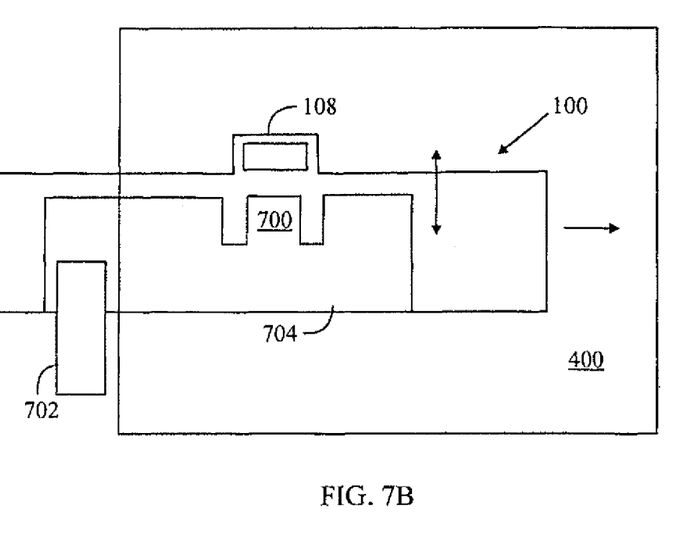
FIG. 7B shows an inlet cleaning mechanism, seen laterally to the ejector.

FIG. 7B shows a cleaning mechanism for the inlet 108, seen laterally to the ejector. The actuator 702 associated with the inlet 108 is not in the combustion chamber 400 but outside it. The projection 700 may be a part of a mechanical structure 704 that may be moved on the outer surface of the outer pipe 106 of the ejector 100. Thus, when the mechanical structure 704 is turned outside the combustion chamber 400, the mechanical structure 704 moves also in the combustion chamber 400, and the projection 700 moves along therewith. The projection 700 may be a claw-like part that is arranged to fit the shape and size of the inlet 108.

Figure 8:
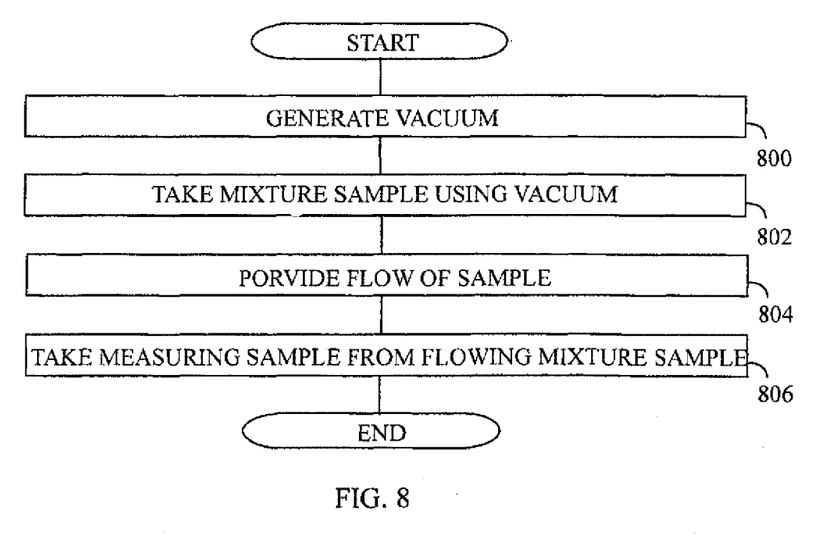
FIG. 8 is a flow chart of the method.

FIG. 8 is a flow chart of the method. In step 800, a vacuum-generating fluid is allowed to flow through an ejector 100 and out via an outlet 116 of the ejector 100 so as to provide vacuum inside the ejector 100. In step 802, a mixture sample 110 is taken, using vacuum, via at least one inlet 108 into the ejector 100 from a mixture 102 of a medium and a solid, the medium being a liquid and/or a gas. In step 804, the mixture sample 110 is brought to flow from an outer pipe 106 along with the vacuum-generating fluid flow through an outlet 116. In step 806, a desired measuring sample 122 is taken into a sample channel 112 from the mixture sample 110 flowing inside the ejector 100 by separating solid particles and a gas or liquid phase from one another in the ejector 100 on the basis of the flow and inertia in the mixture sample 110.

The ejector 100 need not have a mechanical filter at the inlet 108 for filtering large particles from sampling, because apart from the measuring sample 122 both the gas and all the solid particles sucked into the ejector 100 are also blown out of the ejector 100. The measuring sample 122 will not contain much solid particles, or they are below a predetermined limit in size, because the flow of the mixture sample 110 takes the solid particles of highest density and largest size with it and only the measuring sample 122 will enter the sample channel 112.

In the cyclone solution, it is highly likely that solid particles escape from the centre of the ejector 100, because the density of solid particles is higher than that of the gas. In fact, the speed of the turbulent motion determines at least partly how effectively the solid particles disappear from the centre of the ejector, and consequently also how clean the measuring sample 122 to be taken will be. As the speed of the turbulent motion increases, the size of the solid particles appearing in the centre of the ejector 100 is smaller and smaller.

In this manner the filtering is performed dynamically in both impactor-type and cyclone-type sampling without a mechanical filter whose meshes define the largest diameter of solid particles allowed through the filter.

Because there is no need for a filter to prevent solid particles from accessing the measurement, or the filter used has so large meshes that it does not get fouled or blocked and it does not directly define the size of solid particles found in the measuring sample 122, the sampling need not be interrupted to replace or clean the filter. Thus, the sampling may be continuous without interruptions. In addition, several advantages are achieved, because the ejector 100, which takes the mixture sample 110 from the mixture 102 of solid particles and a medium, dynamically filters the mixture sample 110 for a measuring sample 122 into the sample channel 112 and returns the remaining mixture sample 110 into the mixture 102 after sampling the measuring sample 122, is placed in the mixture 102 of solid particles and a medium.

If the mixture sample 110 was not processed on the sampling site, but it would be transferred somewhere outside the mixture 102, the measuring sample 122 might change chemically and structurally. A change may occur as a function of time and/or through an environmental effect. The environmental effect may be a change in temperature, for instance. A change in the mixture sample 110 due to transfer also complicates the processing of the mixture sample 110. For instance, it may become more difficult or impossible to provide a desired measuring sample 122 from the mixture sample 110 for reasons resulting from the transfer. This applies to a measuring sample 122 taken in the combustion chamber 400, for instance.

Whereas, if the mixture sample 110 were not returned back into the mixture 102, a problem would arise where to place the residual mixture sample. Now that it is returned back to where it comes from, no new problem will arise.

Even though the invention is described above with reference to the examples of the attached drawings, it is clear that the invention is not restricted to them, but may be modified in a variety of ways within the scope of the accompanying claims.

The invention claimed is:

1. A sampler, comprising an ejector which is placeable in a combustion chamber and which comprises an inner pipe extending into the ejector to allow a vacuum-generating fluid flow pass through the ejector, and a sample channel which is nested with or adjacent to the inner pipe extending into the ejector and placeable in a mixture of solid particles and a medium, the medium being at least one of the following: a gas, a liquid, the ejector comprises at least one inlet and at least one outlet, the ejector is configured to take a mixture sample by using vacuum via at least one inlet and to discharge the mixture sample via the outlet into the mixture so as to make the mixture sample flow from the inlet towards the outlet and the sample channel is configured to take a desired measuring sample from the mixture sample flowing in the ejector, the solid particles and the medium being at least partly separable from one another in the ejector on the basis of the flow and inertia in the mixture sample.

2. The sampler of claim 1, wherein the sample channel is configured to take a measuring sample from the mixture sample in a direction deviating from the flow direction of the mixture sample so as to render the distribution of solid particles in the measuring sample different from that in the mixture sample.

3. The sampler of claim 1, wherein an end of the sample channel is positioned in the ejector in a location where the distribution of solid particles in the mixture sample is desired due to flow and inertia.

4. The sampler of claim 1, wherein the ejector also comprises an outer pipe, the ejector is configured to allow the vacuum-generating fluid to flow through the inner pipe via the outlet out so as to provide vacuum inside the outer pipe of the ejector, and the ejector is configured to take a mixture sample by using vacuum via at least one inlet into the outer pipe and to discharge the mixture sample, along with the vacuum-generating fluid, via the outlet so as to make the mixture sample flow from the inlet towards the outlet.

5. The sampler of claim 1, wherein the ejector also comprises an outer pipe and the ejector is configured to operate on a cyclone principle in such a manner that the ejector is configured to take a mixture sample by using vacuum onto the outer periphery of the outer pipe so as to bring the mixture sample to turbulent motion inside the outer pipe for separating solid particles from the measuring sample.

6. The sampler of claim 1, wherein the ejector comprises at least one tubular inlet whose central axis orients tangentially to the inner surface of the ejector so as to bring the mixture sample to turbulent motion.

7. The sampler of claim 1, wherein the sampler comprises a fluid channel that is configured to feed dilution fluid into the sample channel.

8. The sampler of claim 1, wherein the combustion chamber is a steam turbine boiler.

9. A method for sampling, comprising:

allowing a vacuum-generating fluid to flow through an ejector in an inner pipe inside the ejector and out via an outlet of the ejector so as to provide vacuum inside the ejector;

taking a mixture sample, using vacuum, via at least one inlet into the ejector that is placed in a combustion chamber from a mixture of a medium and solid particles, the medium being a liquid and/or a gas;

bringing the mixture sample to flow with the vacuum-generating fluid flow through at least one outlet into the mixture; and taking a desired measuring sample into a sample channel nested or parallel with the inner pipe from the mixture sample flowing inside the ejector separating the solid particles and the medium from one another at least partly on the basis of the flow and inertia in the mixture sample.

10. The method of claim 9, wherein the ejector also comprises an outer pipe, further comprising, taking a measuring sample from the mixture sample inside the outer pipe in a direction deviating from the flow direction of the mixture sample so as to render the distribution of solid particles in the measuring sample different from that in the mixture Sample.

11. The method of claim 9, further comprising, positioning an end of the sample channel in the ejector in a location where the distribution of solid particles in the mixture sample is desired due to flow and inertia.

12. The method of claim 9, further comprising, allowing the flow of the vacuum-generating fluid to pass through the inner pipe of the ejector and out via the outlet so as to provide vacuum inside the outer pipe of the ejector; and taking a mixture sample, by using vacuum, via at least one inlet into the outer pipe and discharging the mixture sample, along with the vacuum-generating fluid, via the outlet so as to make the mixture sample flow from the inlet towards the outlet.

13. The method of claim 9, further comprising, bringing the mixture sample to turbulent motion so as to separate solid particles from the measuring sample.

14. The method of claim 9, wherein by bringing the mixture sample to turbulent motion by means of a tubular inlet whose central axis orients tangentially to the inner surface of the ejector.

15. The method of claim 9, further comprising, feeding dilution fluid into the sample channel from a fluid channel.

16. The method of claim 9, wherein the combustion chamber is a steam turbine boiler.

* * * * *